United States Patent [19]

Tarantino et al.

[11] Patent Number: 5,643,800
[45] Date of Patent: Jul. 1, 1997

[54] METHOD OF PREPARING A SAMPLE FOR ANALYSIS BY LASER DESORPTION IONIZATION MASS SPECTROMETRY

[75] Inventors: E. Rocco Tarantino; Scot R. Weinberger, both of Reno, Nev.

[73] Assignee: Hewlett-Packard Company, Palo Alto, Calif.

[21] Appl. No.: 531,431

[22] Filed: Sep. 21, 1995

Related U.S. Application Data

[63] Continuation of Ser. No. 131,789, Oct. 4, 1993, abandoned.
[51] Int. Cl.⁶ ................................................... G01N 33/53
[52] U.S. Cl. .................. 436/518; 436/526; 436/527; 436/531; 436/810; 436/8; 435/4; 435/7.1; 435/970; 427/2.11; 250/288
[58] Field of Search ............................. 436/518, 526, 436/527, 531, 810, 8; 435/4, 7.1, 970; 427/2.11, 350; 422/57, 81, 103; 250/288, 289

[56] References Cited

U.S. PATENT DOCUMENTS

| | | | |
|---|---|---|---|
| 4,461,829 | 7/1984 | Greenquist | 436/530 |
| 4,531,373 | 7/1985 | Rubinsky | 62/63 |
| 4,584,781 | 4/1986 | Parkinson et al. | 34/92 |
| 5,015,845 | 5/1991 | Allen et al. | 250/288 |
| 5,024,830 | 6/1991 | Linner et al. | 424/3 |
| 5,045,694 | 9/1991 | Beavis et al. | 250/287 |
| 5,171,989 | 12/1992 | Williams | 250/288 |
| 5,245,185 | 9/1993 | Busch et al. | 250/288 |
| 5,256,241 | 10/1993 | Noever | 156/600 |
| 5,281,538 | 1/1994 | Cottrell et al. | 436/173 |

OTHER PUBLICATIONS

"Device for Controlling Crystallization of Protein," NASA Tech Briefs, vol. 17, No. 9, Sep. 1993, pp. 92–93.
Preston et al, "Reproducibility and Quantitation of Matrix–assisted Laser Desorption Ionization Mass Spectrometry..." Biol. Mass Spec. vol. 22 (1993), pp. 544–550.
Vorm et al, "Improved Resolution and Very High Sensitivity in MALDI TOF . . . " Anal. Chem. vol. 66 (1994), pp. 3281–3287.

*Primary Examiner*—Carol A. Spiegel

[57] ABSTRACT

The present invention is a sample preparation system and method that can be used with all types of analyte materials, that produces homogeneously deposited crystals across a sample surface, and that lends itself to automation. In this system and method, analyte crystallization is caused by lyophilization. A homogeneous analyte/solvent mixture is placed on a sample surface. The mixture is frozen, then the solvent is sublimated through the application of a vacuum. A homogenous distribution of analyte crystals across the sample surface results.

23 Claims, 4 Drawing Sheets

5,643,800

METHOD OF PREPARING A SAMPLE FOR ANALYSIS BY LASER DESORPTION IONIZATION MASS SPECTROMETRY

This is a continuation of application Ser. No. 08/131,789 filed on Oct. 4, 1993, now abandoned.

BACKGROUND OF THE INVENTION

The present invention relates generally to sample preparation, and more particularly to the preparation of crystallized samples used in scientific measurement instruments.

A source of uncertainty in scientific instrument measurements often lies in the preparation of samples. This is especially true in scientific instruments which use a crystallized analyte or a crystallized mixture of an analyte and a matrix material as a sample. Scientific instruments using crystallized samples perform functions such as mass spectrometry, laser desorption ionization, matrix assisted laser desorption ionization, ionization desorption achieved through fast atom bombardment, ionization desorption achieved through plasma desorption, ionization desorption achieved by electron impact or chemical ionization processes, and electron microscopy. All of these functions are well known to those skilled in the art.

To obtain accurate and reproducible measurements from these instruments, a homogeneous distribution of analyte crystals (or analyte/matrix co-crystals) must be produced on a sample surface. If the crystals are irregularly distributed, it is often necessary to view a magnified image of the sample surface to find a region of relatively evenly distributed crystals suitable for measurement.

Typically, an analyte or an analyte/matrix sample is prepared by first dissolving it into a homogeneous mixture using an aqueous or organic solvent. Such a solvent mixture is required to solvate matrix and analyte molecules, which may possess both hydrophobic and hydrophilic characteristics. Next, the liquid volatile components in a solvent/analyte mixture are removed through the application of heat or vacuum. As will be shown below, neither of these methods is ideal for the preparation of evenly distributed crystals on a sample surface.

For example, the application of heat to biological materials can degrade them, distorting any measurements taken of the biological analyte. Even when a heat tolerant analyte is used, rapid heating can cause boiling, which produces a number of mechanical, convective, and/or conductive perturbations on the sample surface. If the analyte dissolved in the organic solvent begins to crystallize before that which is dissolved in the aqueous, such perturbations can cause a shifting of position and differential deposition of the analyte crystals. The result can be an irregular distribution of analyte crystals upon the sample surface.

Less rapid heating also has its drawbacks when an analyte/matrix solvent mixture is used. If co-crystallization progresses slowly in such a mixture, solvent composition becomes increasingly hydrophilic as the more volatile, organic constituents vaporize. Accordingly, there is a time based crystallization order in which hydrophobic solutes crystalize before hydrophilic solutes. Since most matrix molecules are hydrophobic, they will preferentially co-crystalize with analyte solutes of low hydrophilicity. Thus, problems can occur when analyte solutes of high hydrophilicity are used.

When a vacuum is used to vaporize the liquid volatile solvent components in an analyte/solvent mixture (i.e., the opposing pressure is reduced so that it is less than the vapor pressure of the solvents involved), boiling also occurs. This produces the same mechanical, convective, and/or conductive perturbations on the sample surface as discussed above with respect to boiling caused by heating. Again, an irregular distribution of crystals on the sample surface often results.

An ultrasonic spray and rapid co-crystallization method of sample preparation using a variable vacuum is described in co-pending U.S. application Ser. No. 08/027,317, filed Mar. 4, 1993, and entitled Laser Desorption Ionization Mass Monitor. In this method, a layer of homogenous matrix/analyte solution is applied to a sample surface by an ultrasonic spray apparatus producing a very fine mist. The layer is then crystallized by applying a variable vacuum to the sample surface to remove volatile fluid components. The ability of an operator to view the sample surface and to vary the vacuum applied reduces the mechanical and other perturbations caused by boiling of the volatile liquid solvent components, and results in a more homogeneous distribution of crystals across the sample surface. While such a controlled process provides an improvement over previous sample preparation techniques, the mechanical perturbations inherent in any boiling technique are still present to some degree. Also, this method does not lend itself to automation since a human operator is required to view the sample and to control the vacuum pressure.

U.S. Pat. No. 5,045,694 discloses an electrospray method of applying an analyte/matrix mixture to a sample surface. Although this method appears to produce good quality analyte/matrix crystals, it involves applying a potential of about five thousand volts to the sample surface during application of the layers. This makes the method somewhat hazardous, and can lead to corona discharge between the sample surface and the spray apparatus. This may damage both the sample surface and spray apparatus.

Another method for sample preparation was described in an article entitled "Device for Controlling Crystallization of Protein," NASA Tech Briefs, Vol. 17, No. 9, Sep. 1993, pp. 92–93. In this method, a variable sandwich spacer enables the optimization of the evaporative driving force that governs the crystallization of a protein from solution. The method allows the growth of very large crystals, which are important for applications such as x-ray crystallography. However, this method is expensive since it requires a complex apparatus to be performed. Also, such large crystals are not required for most of the scientific measurement instruments described above.

SUMMARY OF THE INVENTION

Accordingly, it is an object of the present invention to provide an improved sample preparation system and method that can be used with all types of analyte materials, that produces homogeneously deposited crystals across a sample surface, and that lends itself to automation. In this method and system, analyte crystallization is caused by lyophilization. Additional objects and advantages of the invention will be set forth in part in the description which follows, and in part become apparent to those skilled in the art upon examination of the following, or may be learned by practice of the invention. The objects and advantages of the invention may be realized and obtained by means of the instrumentalities and combinations particularly pointed out in the claims.

BRIEF DESCRIPTION OF THE DRAWINGS

The accompanying drawings, which are incorporated in and constitute a part of the specification, schematically illustrate a preferred embodiment of the invention and, together with the general description given above and the detailed description of the preferred embodiment given below, serve to explain the principles of the invention.

DESCRIPTION OF THE PREFERRED EMBODIMENT

Reference will now be made in detail to a preferred embodiment of the invention, which is a system and method for sample preparation. An example of the preferred embodiment is illustrated in the accompanying drawings. While the invention will be described in conjunction with that preferred embodiment, it will be understood that it is not intended to limit the invention to one preferred embodiment. On the contrary, it is intended to cover alternatives, modifications, and equivalents as may be included within the scope of the invention as defined by the appended claims.

As was discussed above, forming crystals from a liquid analyte/solvent mixture often causes unavoidable mechanical and other perturbations which make it difficult to obtain a homogeneous distribution of crystals across a sample surface. However, if crystals can be formed from a solid analyte/solvent mixture by lyophilization, these perturbations can be eliminated, and a more homogeneous distribution of crystals will result. Another advantage of this process is that volatile solvents can be removed from an analyte/solvent mixture without causing heat damage to biological materials.

Lyophilization, or freeze drying, is a process by which volatile components of a frozen mixture are sublimated through the application of a vacuum. This process will withdraw any volatile compound, i.e., a compound whose vapor pressure is significantly higher than the lyophilization pressure.

Figure 1:
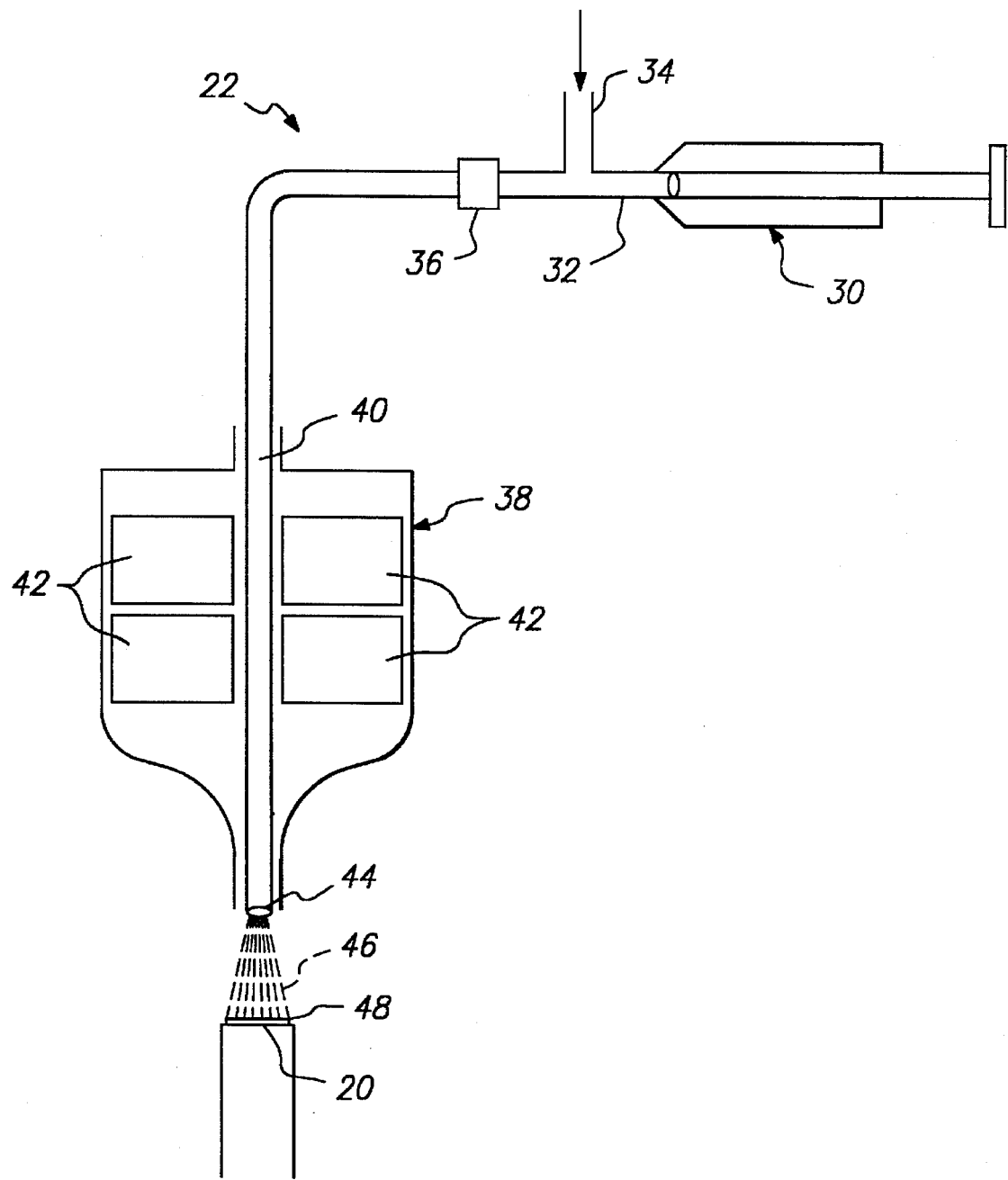
FIG. 1 is a schematic representation of a sample layer being deposited onto a sample surface.

Referring now to FIGS. 1-4, a basic lyophilization process according to the present invention is shown. FIG. 1 shows a sample layer 48 of analyte/solvent mixture being deposited onto a sample surface 20. In one embodiment of the present invention, layer 48 may be deposited onto sample surface 20 by an ultrasonic spray apparatus 22, which is described in the above referenced co-pending U.S. application Ser. No. 08/027,317, and which is incorporated herein by reference.

In ultrasonic spray apparatus 22, a syringe pump 30 contains a solution of matrix material and solvent. The matrix solution is pumped from syringe pump 30 into a conduit 32 which includes an inlet branch 34 through which analyte can be continuously flowed into the matrix solution in the desired proportion. Matrix solution and analyte then enter a vortex micromixer 36 where they are thoroughly mixed. The mixture then flows into an ultrasonic spray module 38. Ultrasonic spray module 38 includes a delivery tube 40 surrounded by one or more piezoelectric ultrasonic transducers 42. Energy from ultrasonic transducers 42 is concentrated into the analyte/matrix/solvent mixture in delivery tube 40, and together with pressure applied by syringe pump 30 causes the mixture to exit a nozzle region 44 as an extremely fine mist 46. The mist is deposited as layer 48 on sample surface 20. Alternatively, ultrasonic spray apparatus 22 may produce an analyte/solvent mist 46, with no matrix material included.

Layer 48 may also be directly deposited onto sample surface 20 using a micropipette (not shown), or any other method by which a homogeneous analyte/solvent mixture can be deposited onto sample surface 20.

Figure 2:
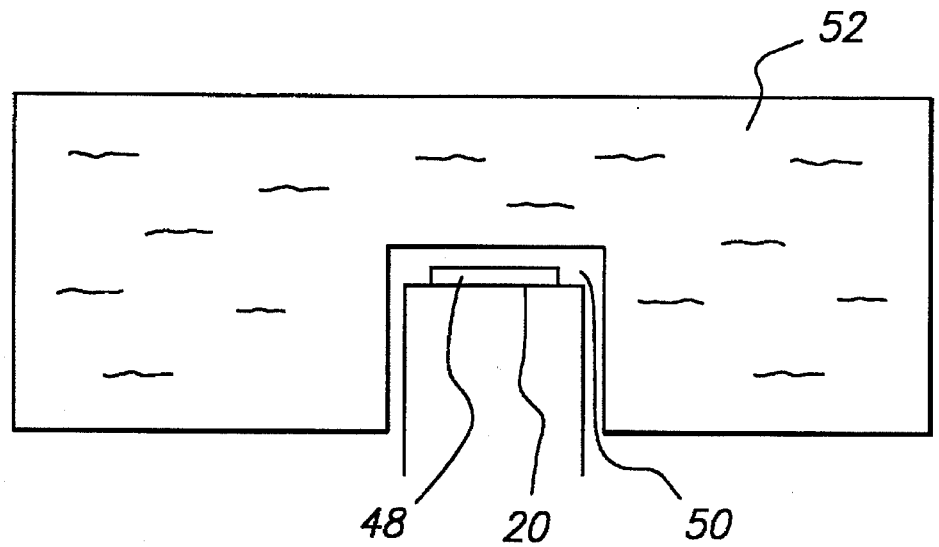
FIG. 2 is a schematic representation of a sample layer being frozen onto a sample surface.

Referring now to FIG. 2, sample layer 48 is next frozen by exposure to extreme cold, preferably below approximately −40° C., −40° most preferably in the range −40° to −200° C. Since sample layer 48 was deposited in the form of a homogeneous liquid, the freezing of sample layer 48 creates a homogeneous distribution of the analyte/solvent mixture across sample surface 20. This freezing step may be performed in a variety of ways. In one embodiment of the present invention, freezing is performed by placing sample layer 48 and sample surface 20 into a freezing chamber 50. Freezing chamber 50 may be cooled by contact with a cold liquid 52, such as liquid nitrogen or a mixture of dry ice and alcohol. As will be apparent to those skilled in the art, sample layer 48 may be frozen by any method that does not physically disturb it.

Figure 3:
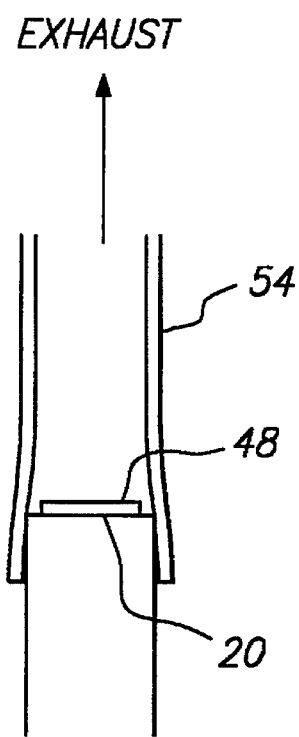
FIG. 3 is a schematic representation of the sublimation of a solvent from a frozen sample layer.

Referring now to FIG. 3, the sublimation of solvent from frozen sample layer 48 will be described. Sample surface 20 and frozen sample layer 48 are next enclosed in a vacuum chamber 54, which is connected to a vacuum pump (not shown). Vacuum chamber 54 may be a vacuum chamber included in the scientific measurement instrument for which the sample is prepared, or it may be a separate vacuum chamber. When chamber 54 is exhausted, the solvent volatiles sublimate from frozen sample layer 48, and the analyte in layer 48 crystallizes on sample surface 28 in a uniform, homogeneous manner. Pressures below approximately 0.1 torr are used. Preferably, pressures in the range from 0.1 to 0.01 torr are used, although lower pressures can be used as well.

Figure 4:
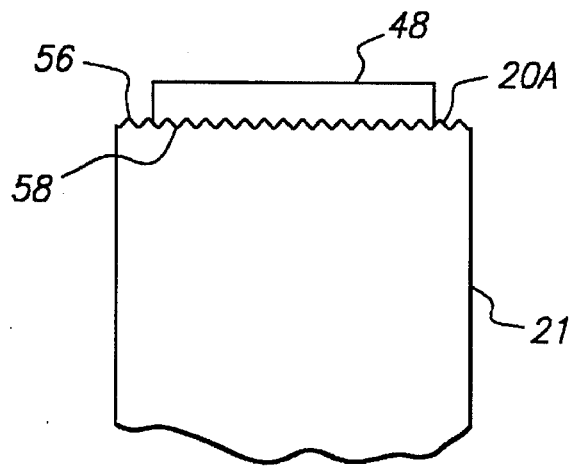
FIG. 4 is a cross sectional view of a roughened sample holder according to the present invention.

In an alternative embodiment of the present invention, the crystallized sample layer 48 can be physically "locked" onto sample surface 20. Referring now to FIG. 4, a cross-sectional view of a "locking" sample holder 21 with a roughened sample surface 20A is shown. Roughened sample surface 20A includes a large number of peaks 56 and depressions 58. The height differential between peaks 56 and depressions 58 is preferably on the order of 1-10 microns. When the liquid analyte/solvent layer 48 is placed onto roughened sample surface 20A, liquid also flows into the crevices created by peaks 56 and depressions 58. Therefore, when sample layer 48 is frozen (as described above), it is held in place by roughened sample surface 20A.

Next, the solvent present in frozen sample layer 48 may be sublimated as described above. The resulting crystals in sample layer 48 allow it to be held in place by roughened sample surface 20A. This embodiment is especially useful in an automated sample preparation system, where the sample surface may be tilted or turned upside down.

Figure 5:
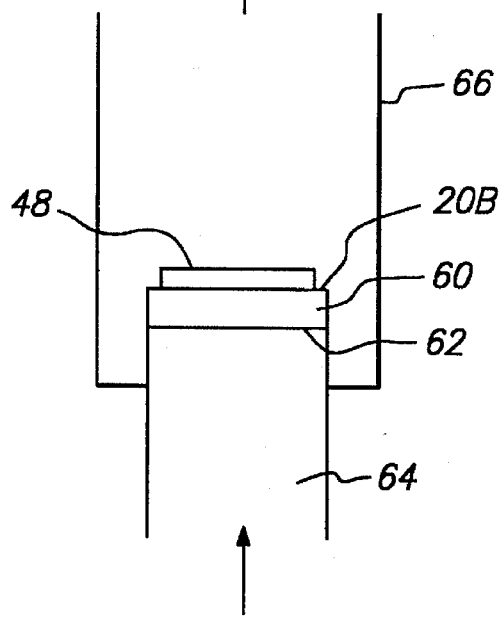
FIG. 5 is a schematic representation of a porus sample surface preparation system according to the present invention.

Referring now to FIG. 5, another method for bonding crystallized analyte to a sample surface is shown. In this method, a porous material is used as the sample surface. This porous material may be made of metal, plastic, or ceramic. For the purposes of this discussion, the porous material will be referred to as a "frit," regardless of the composition of the material.

In one embodiment of the present invention, frit 60 is a flattened piece of material having a sample surface 20B and a second surface 62. Second surface 62 is placed in contact with a tube 64 containing a homogeneous analyte/solvent mixture, and sample surface 20B is exposed to vacuum chamber 66. This mixture is drawn through frit 60 by a partial vacuum created in vacuum chamber 66. When the mixture is drawn through to sample surface 20B, it forms sample layer 48.

In an alternative embodiment, the mixture may be pushed through frit 60 by pressure within tube 64. In yet another alternative embodiment, sample layer 48 may be deposited onto sample surface 20B of frit 60 using either an ultrasonic spray apparatus (see FIG. 1), a micropipette (not shown), or any method by which a homogeneous sample layer 48 may be deposited.

In any embodiment, once a liquid sample layer 48 is formed on sample surface 20B of frit 60, it may be lyophilized as described above. The pores within frit 60 enable the frozen analyte/solvent mixture (and later, the crystallized analyte) to bond with surface 20B. This allows sample surface 20B to be tilted or moved without disturbing sample layer 48.

Figure 6:
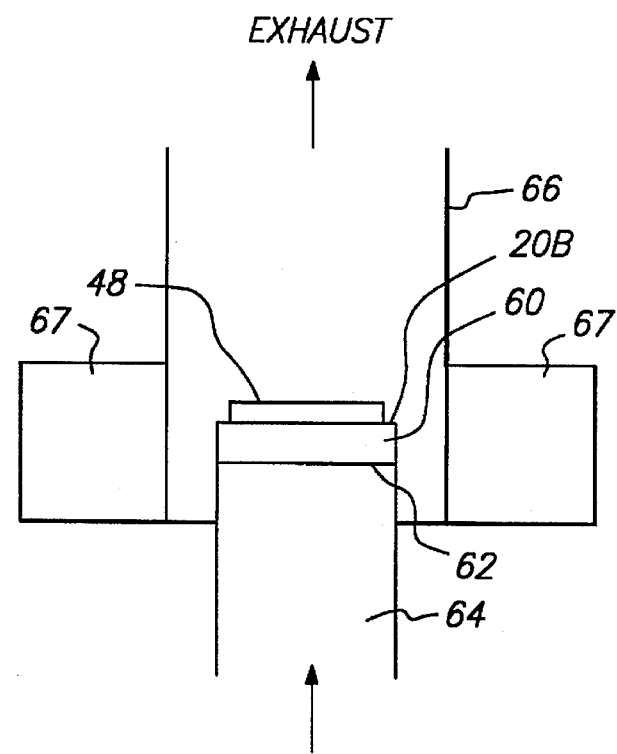
FIG. 6 is a schematic representation of a porus sample surface preparation system according to an alternative embodiment of the present invention.

An additional advantage to using a porous sample surface is that the sample preparation process (including lyophilization) can be partially or completely automated. Referring now to FIG. 6, such a sample automation system is shown. In this system, a liquid sample layer 48 may be formed on sample surface 20B of frit 60 in the same manner as described above with respect to FIG. 5. That is, liquid sample layer 48 may be drawn to sample surface 20B of frit 60 by a partial vacuum within vacuum chamber 66, or by pressure within tube 64. After sample layer 48 is formed, the vacuum within vacuum chamber 66 (or the pressure within tube 64) is stopped to cease the flow of the analyte/solvent mixture onto sample surface 20B.

Next, the liquid sample layer 48 is frozen onto sample surface 20B. As was mentioned above with respect to FIG. 2, there are many methods know to those skilled in the art by which cooling can be provided. In one embodiment of the present invention, cooling may be provided by a cooling jacket 67 which surrounds vacuum chamber 66. Cooling jacket 67 may contain a cold liquid such as liquid nitrogen, or a mixture of dry ice and alcohol.

After sample layer 48 is frozen, vacuum chamber 66 is exhausted. This causes any volatile solvents contained in frozen sample layer 48 to sublimate. Measurements may then be performed on sample layer 48 (if vacuum chamber 66 is part of a measurement instrument), or sample layer 48 (which is bonded to frit 60) may be inserted into a separate measurement instrument.

Yet another advantage to using a porous sample surface is that the surface can be treated with specific binding groups such as ligands or antibodies which add selectivity to the sample preparation technique. A ligand is a chemical compound which functions to bind another chemical compound, or is a group which is bound to a host chemical. Antibodies perform specialized ligand type interactions. These binding groups can be used to search for specific proteins within a complex mixture such as cellular fluids, gastric fluids, digestive fluids, etc.

Figure 7A:
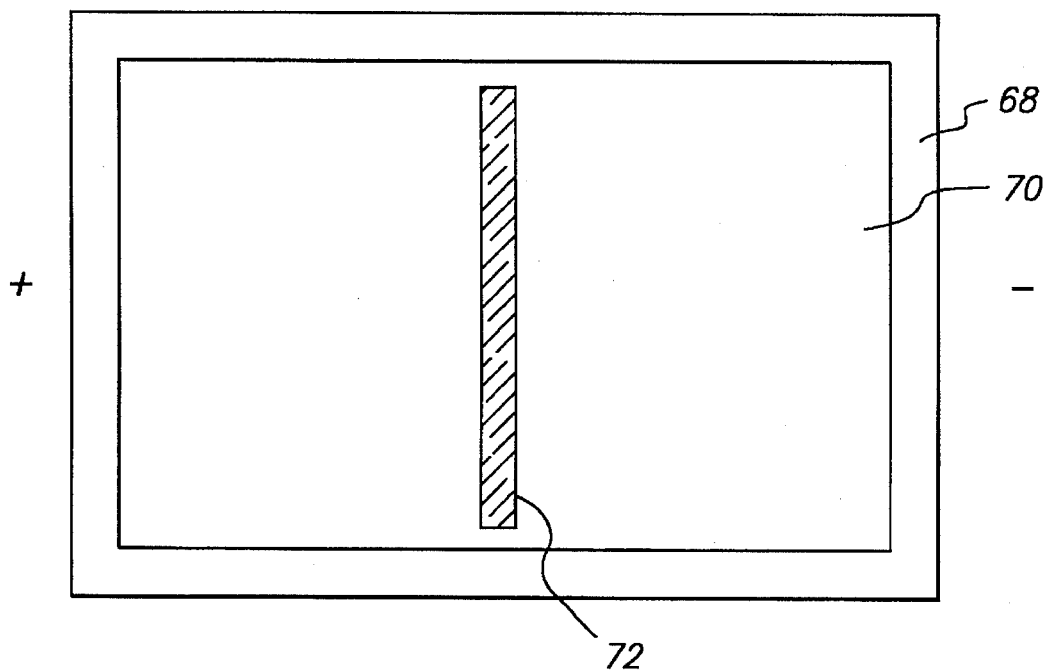
FIGS. 7A and 7B are schematic representations of a combined electrophoresis and lyophilization sample preparation method according to the present invention.
Figure 7B:
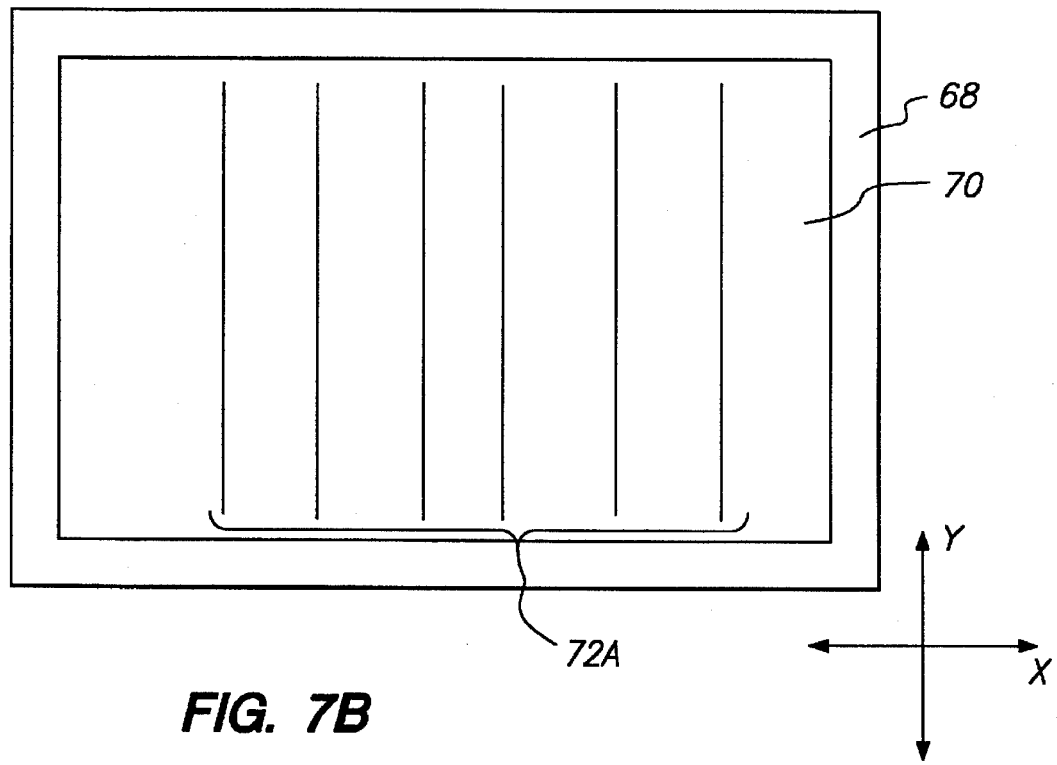

Referring now to FIGS. 7A and 7B, an additional embodiment of the present invention is shown. In this application, which is particularly suited for use in laser desorption ionization mass monitor (LDIM) instruments, two separate analyses can be performed on a protein analyte. A standard electrophoresis analysis is first performed by coating a non-conductive support plate 68 with a polyacrylamide gel 70. A protein analyte 72 is placed in gel 70, and then a voltage is applied across the gel. The electric field created by the applied voltage causes protein components 72A to be separated across the length of the plate 68. Plate 68 is then lyophilized as described above.

After lyophilization, plate 68 can be placed in the vacuum chamber of an LDIM instrument (not shown) where measurements of very precise regions of gel 70 can be taken. To aid in taking measurements across the entire surface of gel 70, plate 68 may be mounted on a mechanism (not shown) which allows it to be translated in two dimensions (X and Y as shown on FIG. 7B). This translation would enable any point on the surface of gel 70 to be sampled by an LDIM instrument.

The present invention has been described in terms of a preferred embodiment. The invention, however, is not limited to the embodiment depicted and described. Rather, the scope of the invention is defined by the appended claims.

What is claimed is:

1. A method for preparing a homogeneous distribution of analyte crystals for analysis in a laser desorption ionization mass monitor, comprising the steps of:

depositing a homogeneous liquid mixture of an analyte and a solvent onto a substantially flat sample surface of a laser desorption ionization mass monitor probe; and lyophilizing said mixture without physically disturbing said mixture in order to produce said homogeneous distribution of the analyte crystals on the probe sample surface.

2. The method of claim 1 wherein said sample surface has a plurality of peaks and depressions, said peaks and depressions having a height differential in the range of 1–10 microns.

3. The method of claim 1 wherein said sample surface is porous.

4. The method of claim 3 further comprising the step of depositing a ligand capable of specifically binding said analyte on said sample surface before said homogeneous liquid mixture depositing step.

5. The method of claim 4 wherein said ligand is an antibody.

6. The method of claim 1 wherein said homogeneous liquid mixture depositing step is performed through application of a mist.

7. The method of claim 1 wherein a micropipette is used to perform said homogeneous liquid mixture depositing step.

8. The method of claim 1 wherein said lyophilization step is performed in a vacuum chamber which is a part of said laser desorption ionization mass monitor.

9. The method of claim 1 wherein said lyophilization step is performed at a temperature below approximately −40° C.

10. The method of claim 1 wherein said lyophilization step is performed at a pressure in the range of approximately 0.01 to 0.1 torr.

11. The method of claim 1 wherein said lyophilization step is performed at a pressure of approximately 0.1 torr.

12. An apparatus for preparing a homogeneous distribution of analyte crystals for analysis in a laser desorption ionization mass monitor, comprising:

a laser desorption ionization mass monitor probe comprising a frit, having a substantially flat sample surface and a second surface;

a tube for depositing a homogeneous liquid mixture of an analyte and a solvent onto said sample surface having an open end placed in contact with said second surface; and a lyophilization means being part of said laser desorption ionization mass monitor and enclosing said sample surface.

13. The apparatus of claim 12 wherein said frit is metallic.

14. The apparatus of claim 12 wherein said frit is ceramic.

15. The apparatus of claim 12 wherein said frit is plastic.

16. The apparatus of claim 12 wherein said lyophilization means comprises a cooling jacket containing liquid nitrogen.

17. The apparatus of claim 12 wherein said lyophilization means comprises a cooling jacket containing a liquid mixture of dry ice and alcohol.

18. A method for preparing homogeneous distributions of analyte crystals for analysis in a laser desorption ionization mass monitor, comprising the steps of:

depositing a layer of polyacrylamide gel onto a nonconductive planar support plate, said plate having a first axis and a second axis;

depositing a protein analyte dissolved in a solvent into said planar gel, said protein analyte including a plurality of protein components;

applying a voltage across a first axis of said planar gel, causing said protein components of said protein analyte to separate along said axis;

lyophilizing said planar gel in the laser desorption ionization mass monitor in order to produce said homogeneous distributions of analyte crystals of said protein analyte components on said planar support plate.

19. The method of claim 18 wherein said lyophilization step is performed by exposing said planar gel and said protein analyte to a temperature below approximately −40° C., and a pressure below 0.1 torr.

20. The method of claim 18 further including the steps of:

translating said planar support plate along its first axis and its second axis so that a specific one of said protein components can be analyzed by said laser desorption ionization mass monitor.

21. A method for preparing a homogeneous distribution of analyte crystals for analysis in a laser desorption ionization mass monitor, comprising the steps of:

forcing a homogeneous mixture of an analyte and a solvent through a porous material, said porous material comprising a laser desorption ionization mass monitor probe having a substantially flat sample surface and a second surface, from the second surface to the sample surface so that a layer of said mixture is formed on said sample surface; and, without physically disturbing said layer, lyophilizing said mixture in order to produce said homogeneous distribution of the analyte crystals on said probe sample surface.

22. The method of claim 21 wherein said forcing step is performed by applying a vacuum to said sample surface, thereby drawing said mixture from said second surface to said sample surface.

23. The method of claim 21 wherein said forcing step is performed by pressurizing said mixture, and applying said pressurized mixture to said second surface so that said mixture flows through said porous material to said sample surface.

* * * * *